United States Patent [19]

Wollweber et al.

[11] 4,127,670

[45] Nov. 28, 1978

[54] 2-FORMAMIDO PHENYLGUANIDINES AND PROCESSES FOR THEIR PREPARATION AND USE

[75] Inventors: Hartmund Wollweber, Wuppertal; Heinrich Kölling, Haan; Herbert Thomas, Wuppertal, all of Germany

[73] Assignee: Bayer Aktiengesellschaft, Germany

[21] Appl. No.: 770,389

[22] Filed: Feb. 22, 1977

[30] Foreign Application Priority Data

Mar. 10, 1976 [DE] Fed. Rep. of Germany ....... 2609994

[51] Int. Cl.² .................. C07C 149/437; A61K 31/27
[52] U.S. Cl. ......................................... 424/300; 560/9; 560/13; 560/25; 560/27
[58] Field of Search ........................... 260/470, 471 C; 424/300; 560/9

[56] References Cited

U.S. PATENT DOCUMENTS

| | | | |
|---|---|---|---|
| 3,812,173 | 5/1974 | Giraudon | 260/471 C |
| 3,828,094 | 8/1974 | Widdig | 260/470 |
| 3,835,164 | 9/1974 | Widdig | 260/471 C |
| 3,869,503 | 3/1975 | Widdig | 260/471 C |
| 3,993,682 | 11/1976 | Kolling | 260/470 |

FOREIGN PATENT DOCUMENTS 2,304,764  8/1974  Fed. Rep. of Germany ....... 260/471 C

*Primary Examiner*—James O. Thomas, Jr.
*Assistant Examiner*—Michael Shippen
*Attorney, Agent, or Firm*—Jacobs & Jacobs

[57] ABSTRACT

N-(2-formamidophenyl)-N',N''-bis-carbonylguanidines bearing an optionally substituted phenoxy, phenylthio, phenylsulfinyl or phenylsulfonyl group in the 4- or 5-position of the 2-(formamido)-phenyl group are anthelminetic agents. The compounds, of which N-(2-formamido-4-phenylthiophenyl)-N',N''-bis-carbomethoxyguanidine is a typical example, are prepared through the reaction of isothiourea-S-alkyl ether and an appropriately substituted 2-aminoformanilide.

3 Claims, No Drawings

2-FORMAMIDO PHENYLGUANIDINES AND PROCESSES FOR THEIR PREPARATION AND USE

DETAILED DESCRIPTION

The present invention pertains to substituted 2-formamidophenylguanidines, to methods for their preparation and use as anthelmintics, and to compositions thereof useful in such use.

Various N-formyl- and N-alkanamido-N',N'''-bis(carbalkoxy)guanidines are described in German Offenlegungschriften Nos. 2,117,293, 2,250,911 and 2,304,764 as having anthelmintic properties. The effect of these properties however is relatively weak. German Offenlegungschrift No. 2,423,679 describes N-(2-alkanamidophenyl)-N',N'''-biscarbonylguanidines bearing a phenoxy, phenylthio, phenylsulfinyl or phenylsulfonyl group in the 4- or 5-position. In these compounds, anthelmintic activity decreases as the number of carbon atoms in the alkanamido group decreases.

The present compounds have significantly higher anthelmintic activity, as much as by a factor of 5 over the closest known compound.

The present invention pertains to anthelmintic phenylguanidines of the formula:

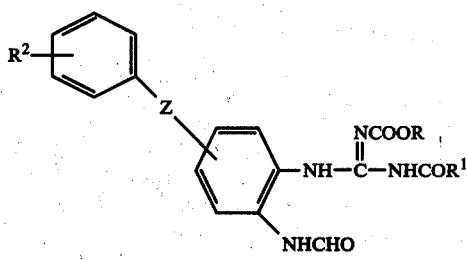

wherein

R is alkyl of 1 to 3 carbon atoms;
$R^1$ is alkyl of 1 to 3 carbon atoms or alkoxy of 1 to 3 carbon atoms;
$R^2$ is hydrogen, fluoro, chloro, methoxy or trifluoromethyl; and
Z is oxygen, sulfur, sulfinyl or sulfonyl.

The foregoing guanidines can de depicted in several tautomeric forms, as shown below for the guanidine moiety only:

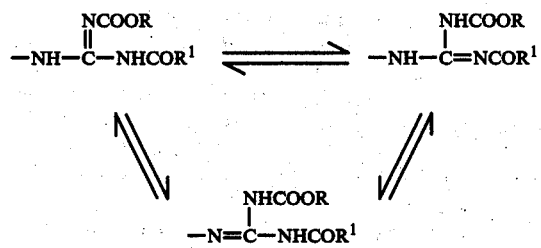

While for consistency and conciseness the structural formulas have been shown in only one of the foregoing ways, it will be appreciated that the actual compounds are inclusive of all tautomeric forms.

In the present context, the optionally-substituted alkyl groups embraced by R and $R^1$ are straight- or branched-hydrocarbon chains containing from 1 to 3 carbon atoms, as for example methyl, ethyl, n-propyl and i-propyl.

Alkoxy groups embraced by $R^1$ will have from 1 to 3 carbon atoms such as methoxy, ethoxy, propoxy and isopropoxy.

A first preferred embodiment pertains to the above compounds wherein $R^2$ is para or meta to Z and Z is para or meta to the depicted guanidine group.

A further preferred embodiment pertains to the above compound wherein R is methyl and $R^1$ is methyl, ethyl, methoxy or ethoxy.

A further preferred embodiment pertains to the above compound wherein $R^2$ is hydrogen.

The compounds are prepared by a process which comprises (a) reacting a compound of the formula:

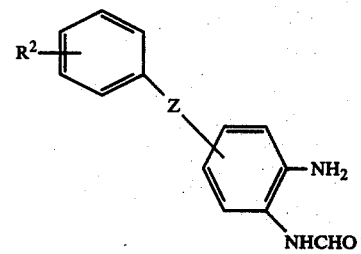

wherein $R^2$ and Z are as defined above, with an isothiourea-S-alkyl ether of the formula:

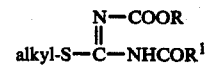

wherein R and $R^1$ are as defined above, in the presence of an acid and in an inert organic solvent, or (b) treating a compound of the formula:

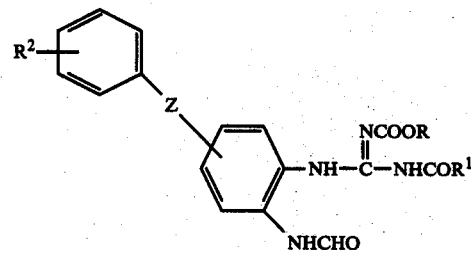

wherein R, $R^1$ and $R^2$ are as defined above and X is sulfur with an oxidizing agent to yield the corresponding compound wherein X is sulfinyl or sulfonyl.

The first of the foregoing two reactions is generally conducted in an inert organic solvent, generally a polar solvent such as an alcohol, as for example methanol, ethanol or isopropanol, a ketone such as acetone or methylethyl ketone, an alkanoic acid such as acetic acid, an ether such as ethyl ether and tetrahydrofuran. The medium may be aqueous, utilizing one of the foregoing water-miscible solvents in combination with water. The reaction is carried out at a temperature of from 0° to 120° C., preferably at normal (room) temperatures; e.g. from about 10° to about 30° C., in the presence of an organic or inorganic acid such as hydrochloric acid, sulfuric acid, nitric acid, formic acid, acetic acid, p-toluenesulfonic acid, and the like. Equimolar amounts of reactants are generally employed although this can vary by about ±20% without significant effect on the yield.

An alkylmercaptan is formed as a by-product and the desired product is obtained by cooling the reaction mixture and collecting the solid which can be purified if desired by conventional techniques such as recrystallization.

In the foregoing second reaction, a compound of the present invention wherein Z is sulfur is treated with one molar equivalent of an oxidizing agent to yield the corresponding compound where Z is sulfinyl or with two moles to yield the corresponding compound where X is sulfonyl. The oxidizing agents include organic peroxoacids, such as peracetic acid, performic acid, perbenzoic acid, m-chlorobenzoic acid, monoperphthalic acid and the like; inorganic peroxides, such as hydrogen peroxide; organic acids dissolved in water or otherwise diluted; inorganic oxidation agents such as chromic acid, nitric acid, potassium permanganate, chlorine or bromine; halo oxy acids such as hypochlorous acid, chlorous acid, chloric acid, perchloric acid, tert.-butyl hypochlorite, methyl hypochlorite, tert.-butylchromate and the like; or N-haloimides such as N-chloro-succinimide and N-bromosuccinimide, N-halo sulphonic acid amides or N-halo carboxylic acid amides.

Reaction conditions are selected, in a manner known to the art, so that oxidation potential is adjusted for the production of either sulfoxides or sulfones.

Many of the thioureas used as starting materials in the first reaction are known (see Olin and Dains, J. Amer. Chem. Soc. 52, 3326 (1930) and U.S. Pat. No. 2,993,502) while others can easily be obtained by known processes. The thioureas are generally prepared from known N-acylthioureas [see, e.g. "Berichte der deutschen Chemischen Gesellschaft", 6, 755 (1873); Ann, Chim. (5) 11, 313 (1877); J. Amer. Chem. Soc. 62, 3274 (1940)], which are reacted with alkylating agents such as alkyl halides, alkyl sulphates or alkyl sulphonates to give the corresponding S-alkyl-N-acyl-isothioureas [see, e.g. J. Org. Chem. 30, 560, (1965); Chem. Pharm. Bull. (Tokyo), 9, 245, (1961)]. These S-alkyl-N-acyl-isothioureas are then reacted with halogenoformic acid esters or with pyrocarbonic acid dialkyl esters [see, e.g. Ber. dtsch, chem. Ges. 71, 1797 (1938)] to give the S-alkyl-N-acyl-N'-alkoxycarbonyl-isothioureas, which corresponds to the known substitution of S-alkyl-isothioureas with chloroformic acid alkyl esters [see, e.g. J. Amer. Chem. Soc. 52, 3326 (1930)].

The following are typical isothioureas which can be employed in accordance with the process of this invention: N,N'-bis-methoxycarbonyl-S-methyl-isothiourea (melting point 99°-100° C.), N,N'-bis-ethoxycarbonyl-S-methyl-isothiourea (melting point 50°-51° C.), N-ethoxycarbonyl-N'-propionyl-S-methyl-isothiourea (melting point 92°-94° C.), N-methoxycarbonyl-N'-propionyl-S-methyl-isothiourea (melting point 97°-99° C.) and N-methoxycarbonyl-N'-ethoxyacetyl-S-methylisothiourea (melting point 69°-70° C.)

The 2-aminoformanilide starting materials are known and in any event can be readily prepared by methods analogous to those disclosed in the literature. For example, a 2-nitroaniline having the appropriate substituent in the 4- or 5-position; e.g., phenoxy, phenylthio, phenylsulfinyl or phenylsulfonyl, can be treated with formic acid to yield the corresponding 2-nitro-4- or 5-substituted formanilide which is hydrogenated as with Raney nickel to yield the 2-amino-4- or 5-substituted formanilide. The 2-nitroformanilines having a phenylsulfinyl or phenylsulfonyl group in the 4- or 5-positions can also be obtained from the corresponding phenylthio compounds through controlled oxidation analogous to that described above; e.g. using hydrogen peroxide in acetic anhydride or perbenzoic acid in dioxane or chloroform, to yield the sulfinyl compound, or hydrogen peroxide in glacial acetic acid to yield the sulfone. The 4- and 5-phenylsulfonyl-2-nitroanilines can also be obtained by the reaction of a sodium benzenesulfinate with a 4- or 5-chloro-2-nitroaniline as for example dimethylformamide at about 140° C.

Typical 2-aminoformanilide starting materials include: 2-amino-5-phenylthioformanilide, 2-amino-5-phenylsulfinylformanilide, 2-amino-5-phenylsulfonylformanilide, 2-amino-5-phenoxyformanilide, 2-amino-5-(4-fluorophenylthio)formanilide, 2-amino-5-(3-methoxyphenylthio)formanilide, 2-amino-5-(3-trifluoromethylphenylthio)formanilide, 2-amino-5-(3-chlorophenylthio)formanilide, 2-amino-5-(4-fluorophenylsulfinyl)formanilide, 2-amino-4-phenylthioformanilide, 2-amino-4-phenylsulfinylformanilide and 2-amino-4-phenylsulfonylformanilide.

The following compounds are representative embodiments of the invention: N-(2-formamido-4-phenylthiophenyl)-N',N''-bis(carbomethoxy)guanidine, N-(2-formamido-4-phenylthiophenyl)-N',N''-bis(carbethoxy)guanidine, N-(2-formamido-4-phenylthiophenyl)-N'-carbomethoxy-N''-propionylguanidine, N-(2-formamido-4-phenylsulfinylphenyl)-N',N''-bis(carbomethoxy)guanidine, N-(2-formamido-4-phenylsulfinylphenyl)-N',N''-bis(carbethoxy)guanidine, N-(2-formamido-4-phenylsulfonylphenyl)-N',N''-bis(carbomethoxy)guanidine, N-(2-formamido-4-phenylsulfonylphenyl-N'-carbethoxy-N''-carbomethoxyguanidine, N-(2-formamido-4-phenoxyphenyl)-N',N''-bis(carbomethoxy)guanidine, N-(2-formamido-4-phenoxyphenyl)-N',N''-bis(carbethoxy)guanidine, N-(2-formamido-5-phenylsulfonylphenyl)-N',N''-bis(carbomethoxy)guanidine, N-(2-formamido-5-phenylthiophenyl)-N',N''-bis(carbomethoxy)guanidine and N-(2-formamido-5-phenylsulfonylphenyl)-N',N''-bis(carbomethoxy)guanidine.

The compounds prepared in accordance with the invention show a surprisingly improved action against one or more of the following nematodes and cestodes:

Hookworms (for example *Uncinaria stenocephala, Ancylostoma caninum* and *Bunostomum trigonocephalum*).

Trichostrongylidae (for example *Nippostrongylus muris, Haemonchus contortus, Trichostrongylus colubriformis* and *Ostertagia circumcincta*).

Strongylidae (for example *Oesophagostomum columbianum*).

Rhabditidae (for example *Strongyloides ratti*).

Ascaridae (for example *Ascaris suum, Toxocara canis* and *Toxascaris leonina*).

Threadworms (for example *Aspiculuris tetraptera*).

Heterakidae (for example *Heterakis spumosa*).

Whipworms (for example *Trichuris muris*).

Filariae (for example *Litomosoides carinii* and *Dipetalonema witei*).

Cestodes (for example *Hymenolepis nana, Taenia pisiformis* and *Echinococcus multilocularis*).

The action of the compounds of the invention can be conveniently observed in vivo by oral and parenteral administration to test animals heavily infested with parasites.

Stomach and intestine worm test/sheep

Sheep experimentally infected with *Haemonchus contortus* or *Trichostrongylus colubriformis* were treated after the end of the pre-patency period of the parasites. The pure active compound was administered orally in gelatin capsules. The effectiveness is determined by quantitatively counting the worm egs, excreted with the faeces, before and after the treatment. Complete cessation of the excretion of eggs after the treatment denotes that the worms have been expelled or have been so damaged that they can no longer produce any eggs (effective dose).

The compounds tested and the minimum effective dose are shown below.

Table I

| Compound | Note | Min. Effective Dose (90%) mg/kg | |
|---|---|---|---|
| | | Haemonchus cont. | Trichostrongylus col. |
| N-(2-formamido-4-phenylthiophenyl)-N',N''-bis-(carbomethoxy)guanidine | 1 | 0.5 | 0.5 |
| N-2-acetamidophenyl-N',N'-bis(carbomethoxy)guanadine | 2 | 100 | 50 |
| N-2-propanamidophenyl-N',N''-bis(carbomethoxy)guanidine | 2 | 50 | 10 |
| N-(2-butanamido-4-butylphenyl)-N',N'-bis(carbomethoxy)guanidine | 3 | 10 | 5 |
| N-(2-butanamido-5-benzoylphenyl-N',N'-bis(carbomethoxy)guanidine | 3 | 5 | — |
| N-(2-acetamido-4-phenylthiophenyl-N',N'-bis(carbomethoxy)quanidine | 4 | 2.5 | 2.5 |

Notes
1 = present invention
2 = German O.S. 2,117,293
3 = German O.S. 2,250,911
4 = German O.S. 2,423,679

The compounds of the invention are employed to combat helmintic infestations, both prophylactically and therapeutically, in humans and other animals through administration thereto of an anthelmintically effective amount of one or more compounds. Generally such an amount will range from about 0.1 mg/kg to about 50 mg/kg of body weight, depending upon the stage and severity of the infestation. This range is of course merely a guideline and the actual dose should be titrated to the recipient keeping in mind his age, general health and body weight, the response to treatment and the type of formulation. At times less than 0.1 mg/kg will suffice while at others more than 50 mg/kg can be indicated. The total daily dose thus will generally be from about 5 mg to about 5 g, although here again this is merely a guideline.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following examples will serve to further illustrate the compound of the invention and the methods of preparation without being a limitation on the scope thereof, the scope being defined solely by the appended claims.

EXAMPLE 1

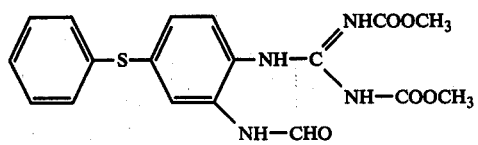

19.9 g (0.0815 mol) of 2-amino-5-phenylthioformanilide in 350 ml of methanol and 9.5 ml of glacial acetic acid are stirred with 18.1 g (0.088 mol) of N,N'-bis(carbomethoxy)isothiourea S-methyl ether for 15 hours at room temperature. After the mixture has cooled, the precipitate is removed by filtration, washed with ether and recrystallized from ethyl acetate. 17 g of N-(2-formamido-4-phenylthiophenyl)-N',N''-bis(carbomethoxy)guanidine, m.p. 152° C., are obtained.

2-Amino-5-phenylthioformanilide, m.p. 118° C., used as the starting material, is obtained by catalytic hydrogenation of 2-nitro-5-phenylthioformanilide, m.p. 108° C. 2-Nitro-5-phenylthioformanilide, in turn, is prepared by reacting 2-nitro-5-phenylthioaniline with formic acid.

EXAMPLE 2

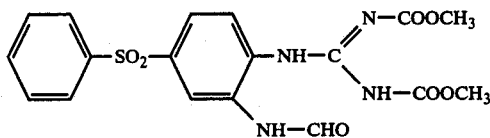

25.1 g of N-(2-formamido-4-phenylthiophenyl)-N',N''-bis(carbomethoxy)guanidine (Example 1) are dissolved in 650 ml of acetic anhydride. 42 g of hydrogen peroxide (30% strength) are added and the mixture is stirred overnight and evaporated in vacuo. The residue crystallizes after trituration with a mixture of ethyl acetate and ether. The product is collected by filtration and recrystallized from ethyl acetate to yield N-(2-formamido-2-phenylsulfonylphenyl)-N',N''-bis(carbomethoxy)guanidine (22.2 g), m.p. 175° C. (dec.).

EXAMPLE 3

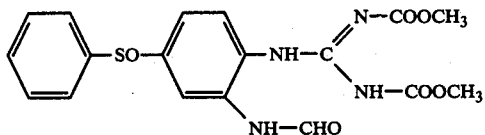

10.9 g of N-(2-formamido-4-phenylthiophenyl)-N',N''-bis(carbomethoxy)guanidine (Example 1) are dissolved in 200 ml of acetic anhydride. 25.8 ml of hydrogen peroxide (30% strength) are added and the mixture is stirred for 4 hours at 20° and is then concentrated in vacuo, and the residue is recrystallized from ethyl acetate to yield N-(2-formamido-4-phenylsulfinylphenyl)-N',N''-bis(carbomethoxy)guanidine (7.37 g), m.p. 168° C. (dec.).

EXAMPLE 4

By separating substituting N-carbomethoxy-N'-carbethoxyisothiourea S-methyl ether and N-carbomethoxy-N'-propionylisothiourea S-methyl ether and N,N'-bis(carbomethoxy)isothiourea-S-methyl ether in the procedure of Example 1, there are respectively obtained N-(2-formamido-4-phenylthiophenyl)-N'-carbomethoxy-N''-carbethoxyguanidine, m.p. 143° C. (dec.), N-(2-formamido-4-phenylthiophenyl)-N'-carbomethoxy-N''-propionylguanidine, m.p. 126° C. (dec.) and N-(2-formamido-4-phenylthiophenyl)-N',N''-bis(carbethoxy) guanidine.

EXAMPLE 5

By separately substituting 2-amino-4-phenylthioformanilide, 2-amino-5-phenoxyformanilide, 2-amino-5-phenylsulfinylformanilide and 2-amino-5-phenylsulfonylformanilide in the procedure of Example 1, there are respectively obtained N-(2-formamido-5-phenylthiophenyl)-N',N''-bis(carbomethoxy)-guanidine, m.p. 159° C. (dec.), N-(2-formamido-4-phenoxyphenyl)-N',N''-bis(carbomethoxy)guanidine, m.p. 173° C. (dec.), N-(2-formamido-4-phenylsulfinylphenyl)-N',N''-bis(-carbomethoxy)guanidine, m.p. 168° C. (dec.), and N-(2-formamido-4-phenylsulfonylphenyl)-N',N''-bis(carbomethoxy)guanidine, m.p. 175° C. (dec.).

EXAMPLE 6

In a similar fashion, the following formanilides are substituted in the procedure of Example 1:
2-amino-5-(4-fluorophenylthio)formanilide,
2-amino-5-(3-chlorophenylthio)formanilide,
2-amino-5-(3-methoxyphenylthio)formanilide,
2-amino-5-(3-trifluoromethylphenylthio)formanilide, and
2-amino-5-(4-fluorophenylsulfonyl)formanilide.
There are thus respectively obtained:
N-[2-formamido-4-(4-fluorophenylthio)phenyl]-N',N''-bis(carbomethoxy)guanidine,
N-[2-formamido-4-(3-chlorophenylthio)phenyl]-N',N''-bis(carbomethoxy)guanidine,
N-[2-formamido-4-(3-methoxyphenylthio)phenyl]-N',N''-bis(carbomethoxy)guanidine,
N-[2-formamido-4-(3-trifluoromethylphenylthio)phenyl]-N',N''-bis(carbomethoxy)guanidine, and
N-[2-formamido-4-(4-fluorophenylsulfonyl)phenyl]-N',N''-bis(carbomethoxy)guanidine.

Likewise by substituting:
2-amino-4-phenylsulfinylformanilide,
2-amino-4-phenylsulfonylformanilide, and
2-amino-4-phenoxyformanilide,
there are respectively obtained:
N-(2-formamido-5-phenylsulfinylphenyl)-N',N''-bis(-carbomethoxy)guanidine,
N-(2-formamido-5-phenylsulfonylphenyl)-N',N''-bis(-carbomethoxy)guanidine, and
N-(2-formamido-5-phenoxyphenyl)-N',N''-bis(carbomethoxy)guanidine.

EXAMPLE 7

Substituting N-carbomethoxy-N'-acetylisothiourea S-methyl ether in the procedure of Example 1 yields N-(2-formamido-4-phenylthiophenyl)-N'-carbomethoxy-N''-acetylguanidine.

EXAMPLE 8

A typical preparation of the starting formamides is as follows: 2-amino-4-phenylthioformanilide, m.p. 117° C., can be prepared by catalytic hydrogenation of 2-nitro-4-phenylthioformanilide, m.p. 133° C. 2-Nitro-4-phenylthioformanilide can be prepared by reacting 2-nitro-4-phenylthioaniline with formic acid. 2-Nitro-4-phenylthioaniline, m.p. 81° C., can be prepared by treating a solution of 1-chloro-2-nitro-4-phenylthiobenzene in dioxane with ammonia under pressure at 160° C. 1-Chloro-2-nitro-4-phenylthiobenzene, m.p. 43° C., can be prepared by reacting 4-chloro-3-nitrobenzenediazonium chloride with sodium thiophenolate. The product is purified by column-chromatography ($Al_2O_3$ III/eluent: petroleum ether).

What is claimed is:

1. The compound N-(2-formamido-4-phenylthiophenyl)-N',N''-bis(carbomethoxy)guanidine.

2. A pharaceutical composition comprising an anthelmintically effective amount of the compound according to claim 1 and a pharmaceutically acceptable carrier.

3. The method of combatting helmintic infestation in humans and animals which comprises administering to a human or animal an anthelmintically effective amount of the compound according to claim 1.